US00H002090H

(19) United States

(12) Statutory Invention Registration (10) Reg. No.: US H2090 H

Walker (43) Published: Nov. 4, 2003

(54) ONE-PIECE UNITARY OCCLUDER

(75) Inventor: Clarence L. Walker, Manchester, MO (US)

(73) Assignee: Sherwood Services, A.G., Schaffausen (CH)

(21) Appl. No.: 09/460,314

(22) Filed: Dec. 13, 1999

(51) Int. Cl.[7] ..... A61M 1/00

(52) U.S. Cl. ..... 604/153; 604/151

(58) Field of Search ..... 604/153, 151

(56) References Cited

U.S. PATENT DOCUMENTS

| | | | | | |
|---|---|---|---|---|---|
| 4,689,043 | A | * | 8/1987 | Bisha | 604/250 |
| 4,913,703 | A | * | 4/1990 | Pasqualucci et al. | 604/153 |
| 5,145,693 | A | * | 9/1992 | Hinzpeter et al. | 425/149 |
| 5,171,301 | A | * | 12/1992 | Vanderveen | 604/141 |

* cited by examiner

*Primary Examiner*—Michael J. Carone
*Assistant Examiner*—M. Thomson

(74) *Attorney, Agent, or Firm*—Lewis, Rice & Fingersh, L.C.

(57) ABSTRACT

A one-piece unitary occluder is disclosed which is utilized with a fluid administration set to occlude a portion of a tube assembly which is interconnected between a source of fluid and a patient. The one-piece unitary occluder has a body with a pair of openings which are diametrically aligned with an aperture to allow fluid flow therethrough; however, once activated, the openings are misaligned relative to the aperture to occlude a portion of the tubing to prevent fluid free-flow if the tube assembly becomes disassociated from the pump.

17 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ONE-PIECE UNITARY OCCLUDER

BACKGROUND OF THE INVENTION

1. Field of the Invention

The present invention relates to fluid administration systems, and more particularly to fluid administration systems having an occluder adapted to prevent fluid free-flow. More specifically, the present invention relates to a one-piece unitary occluder for use with a pump of a fluid administration system which is connected to a tube assembly and adapted to prevent fluid free-flow therethrough.

2. Prior Art

Administering fluid containing medicine or nutrition to a patient is generally well-known in the art. Typically, the fluid is supplied to a patient by a tube assembly which interconnects a fluid source to a patient. The fluid is supplied to the patient through either an enteral connection which accesses a visceral organ (gastrointestinal feeding), or through a parenteral connection which accesses a non-visceral organ (intravenous feeding).

The fluid flow rate through the tube assembly is typically controlled by a mechanical clip which is designed to progressively occlude the tube and selectively impede the fluid flow induced by gravity. One such mechanical clip which operates to occlude a portion of the tube is a conventional roller clamp that has a hollow body with opposed openings and a pair of angled slots opposite one another which are formed transverse to the openings. The clip further includes a wheel having an axle which is coupled to the body with the axle fitted within the slots. The tube is the inserted through the openings and the wheel is rolled along the slots to pinch a portion of the tube against the body which progressively occludes the tube. Although devices of the above-mentioned character operate to provide a cost-efficient method for controlling the flow rate, these devices must be manually actuated. Further, another drawback is that the wheel may be inadvertently bumped or jostled out of position resulting in an inappropriate flow rate.

In order to enhance flow-rate control, calibrated pumps have been found to be useful. One such pump that has been used in the art is a peristaltic pump connected in-line along a portion of the tube between the fluid source and the patient. The pump advances the fluid through the tube by occluding successive portions of the tube and then urging each occluded portion forward. When a pump is utilized to control the flow rate, mechanical clips are typically not employed or are disengaged to prevent the clamp from interfering with the flow rate.

Peristaltic pumps are generally classified as being either a rotary, such as the device described in U.S. Pat. No. 4,913,703 to Pasqualucci et al. entitled "Safety Interlock System for Medical Fluid Pumps", or linear, such as the device described in U.S. Pat. No. 4,493,706 to Borsangi entitled "Linear Peristaltic Pumping Apparatus and Disposal Cassette Therefore", both of which are incorporated herein by reference. Generally, rotary peristaltic pumps have a motor driver rotor mounted on a surface of the pump which carries two or more circumferentially spaced apart rollers designed to occlude a portion of the tube. As the motor rotates the rotor, the spaced apart rollers are sequentially brought into contact with, and occlude, portions of the tube. A predetermined volume of fluid is contained between each of the occluded portions so that this measured volume of fluid is advanced through the tube.

Rotary peristaltic pumps can be further subclassified as being either clinical, for use with bedridden patients, or ambulatory, for use with patients that have some degree of mobility. The '703 patent describes a representative clinical pump having a tubing assembly with a pair of members each receivable within a corresponding recess. The tube assembly is engaged with the pump by coupling the first member with the corresponding recess, stretching the tube around the rotor, and then coupling the second member with the other recess. In contrast, ambulatory peristaltic pumps, such as that described in U.S. Pat. No. 5,181,842 granted to Sutherland, et al. entitled "Peristaltic Infusion Device", include a battery operated pump for use by patients who are capable of some degree of mobility. These peristaltic pumps have a rotor member and a swing arm rotatably mounted adjacent to the rotor. The arm is movable between an open position and a closed position. In the open position, the tube assembly is slack to simplify threading it about the rotor. Then the swing arm is biased into the closed position to automatically align and stretch the tube around the rotor by the arm.

Although clinical and ambulatory peristaltic pumps have substantially improved the art, one drawback found with such devices is that once the tube assembly is disengaged, either intentionally or unintentionally from the pump, the flow rate is unrestrained as the fluid is drawn through the tube due to gravity. This situation is known as fluid free-flow and may present an undesirable, or even life threatening situation, if undetected because of the risk of overfeeding or overmedicating a patient.

In order to overcome the above-noted drawbacks to fluid administration systems utilizing pumps, several devices have been suggested which operate to automatically occlude a portion of the tube and prevent fluid free-flow if the tube becomes disengaged from the pump while also permitting uninhibited fluid flow when the assembly is properly engaged to the pump. For instance, a variety of automatic occluders have been suggested to improve the art such as the device disclosed in U.S. Pat. No. 4,689,043 to Bisha entitled "IV Tube Activator" which describes a clamp for use with a peristaltic pump. The clamp includes a V-shaped channel which is spring biased into a closed position where the narrow portion of the V-shaped channel is sized to substantially crimp, or occlude, a portion of the tube and prevent fluid flow therethrough. The clamp may be urged into an open position by a handle which overlays the pump and depresses the springs such that the tubing is positioned within the wider portion of the V-shaped channel to permit unrestricted flow through the tubing. If the handle is released either intentionally or unintentionally, the V-shaped portion will automatically slide into the closed position and prevent fluid free-flow by crimping or occluding a portion of the tubing assembly.

Another automatic occluder is disclosed in U.S. Pat. No. 5,704,582 to Winterer, et al. entitled "Pinched Clipped Occluder for Infusion Sets" which describes a clip that is positioned between a housing and a cover of a pump. The clip has a plunger biased by a spring towards a portion of the tube so that the tubing may be occluded. Fluid flow through the tube may only be established when the plunger is biased away from the tube which occurs when the cover is properly coupled with the housing. However, once the cover becomes disengaged from the housing, the plunger is automatically biased into the closed position by the spring to prevent fluid free-flow.

Although both of the aforementioned automatic occluders have advanced the art, both devices are mechanically complex and prone to mechanical failure. In addition, the mechanical complexity also results in occluders which are expensive to manufacture.

Accordingly, one skilled in the art can best appreciate that several advances would be still be desirable. For instance, it would be desirable to have a fluid administration system which has an automatic occluder capable of preventing fluid free-flow through a portion of the tube. In addition, it would also be desirable to have an occluder which has a one-piece unitary design.

OBJECTS AND SUMMARY OF THE INVENTION

In brief summary, the present invention overcomes and substantially alleviates the deficiencies present in the art by providing a one-piece unitary occluder for a fluid administration system which is adapted to prevent fluid free-flow. The one-piece unitary occluder is used in a fluid administration system having a pump connected in-line along a tube assembly.

Generally, the pump includes a body having a pair of shoulders and a recess formed therein. Extending from the body is a rotor while a cover is pivotably attached to the body over the rotor. The tube assembly includes three interconnected tube segments each having a distal end and a proximal end. A fluid source is connected to the distal end of the first tube segment while the proximal end of the first tube segment is connected to the distal end of the second tube segment by a drip chamber having an abutment surface. The proximal end of the second tube segment is interconnected to the distal end of the third tube segment by a coupling having an external flange. Finally, the proximal end of the third tube segment is connected to a patient.

The tube assembly is engaged with the pump by threading the assembly around the rotor with the abutment surface and external flange engaged with the first shoulder and second shoulder, respectively. The abutment surface is spaced apart from external flange by the length of the second tube segment. Preferably, this length permits the abutment surface and the external flange to be properly captured by the first and second shoulders, respectively, while stretching the second tube segment about the rotor. Finally, each of the tube segments have a lumen to allow the passage of fluid therethrough.

One unique aspect of the one-piece unitary occluder is that it is fitted within the recess of the pump. Unlike prior art occluders which include multiple separate elements, the one-piece unitary occluder of the present invention has a generally cylindrical shape formed from a single sheet of material having proximal and distal ends defining first and second openings, respectively, at least partially overlapping one another and an aperture disposed therebetween. Each of the openings and the aperture are sized to receive a portion of the tube assembly therethrough. Adjacent the first opening is a pair of hooks adapted to engage the second opening and maintain the unitary occluder in its generally cylindrical shape with both openings in an aligned configuration relative to the aperture which is located diametrically across from the openings.

The one-piece unitary occluder also includes a V-shaped bend proximate the distal end thereof adapted to spring radially outwardly away from the proximal end once the hooks are released from the second opening so that the occluder is capable of uncoiling and misaligning the first and second openings relative to the aperture. When the occluder uncoils from its generally circular configuration the portion of the tube assembly which extends through the first and second openings and the aperture of the one-piece unitary occluder is occluded to prevent fluid free-flow through the assembly. The one-piece unitary occluder is fitted within the recess of the pump such that a portion of the occluder extends upwardly away from the body. When the cover is pivoted into a closed position, the cover abuts and biases the occluder to disengage the hooks from the second opening while also maintaining the alignment between both opposed openings and the aperture. However, once the cover of the pump is moved into an open position, the occluder springs into the misaligned position with each opening being misaligned relative to the aperture in order to prevent fluid flow through the tube assembly.

To manufacture the occluder of the present invention, a body is cut from a flat sheet or band of suitable metallic material. First and second openings are then punched through the body proximate the distal and proximal ends, respectively, while an aperture is concurrently punched through the body between the first and second openings. After the aperture and openings are punched through the body, a circumferential shoulder is formed about the aperture extending upwardly from the body, while a pair of tabs are formed proximate the first opening and then bent downward from the body to form hooks. The second end portion is bent into a substantially V-shaped configuration. Finally, the body is rolled into a substantially cylindrical shape with the distal end overlaid by the proximal end with the hooks extending outwardly from the body and capturing the second opening as the shoulder extends inwardly.

In operation, the user of the present invention places the one-piece unitary occluder about a portion of the tube assembly such that a portion of the tube assembly is threaded through the aperture and the pair of openings. The abutment surface of the drip chamber is then engaged with the first shoulder and the second tube segment is wrapped about the rotor of the pump. The user then stretches the second tube segment so that the coupling may be engaged with the second shoulder. Finally, the one-piece unitary occluder is fitted into the recess such that a portion of the occluder extends upwardly away from the body of the pump.

While the hooks are engaged with the second opening, the first and second openings of the one-piece occluder are retained in alignment relative to the aperture so that the third tube segment is not crimped, or occluded, by misalignment of the openings. Once the cover is oriented in the closed position, the exposed portion of the occluder is contacted by the cover and forced to bias inwardly upon itself such that the hooks are released from engagement with the second opening. After the hooks disengage the second opening, the one-piece occluder is maintained in an orientation with both first and second openings aligned relative to the aperture since the occluder is biased by the cover. However, if the cover happens to be disassociated from the housing the one-piece occluder automatically biases outwardly in order to misalign the first and second openings relative to the aperture, thereby occluding the tube assembly and prevent fluid flow therethrough.

Accordingly, the primary object of the present invention is to provide a one-piece unitary occluder adapted to prevent fluid-free flow in a fluid administration system having a pump which is connected in-line along a tube assembly.

Another object of the present invention is to provide an occluding device which minimizes the opportunity for mechanical failure during operation.

A further object of the present invention is to provide an occluding device that is inexpensive to manufacture.

These and other objects of the present invention are realized in the preferred embodiment of the present invention, described by way of example and not by way of limitation, which provides for a one-piece unitary occluder which is adapted to automatically occlude a portion of a tube assembly to prevent fluid free-flow whenever the tube assembly becomes disassociated from the pump.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
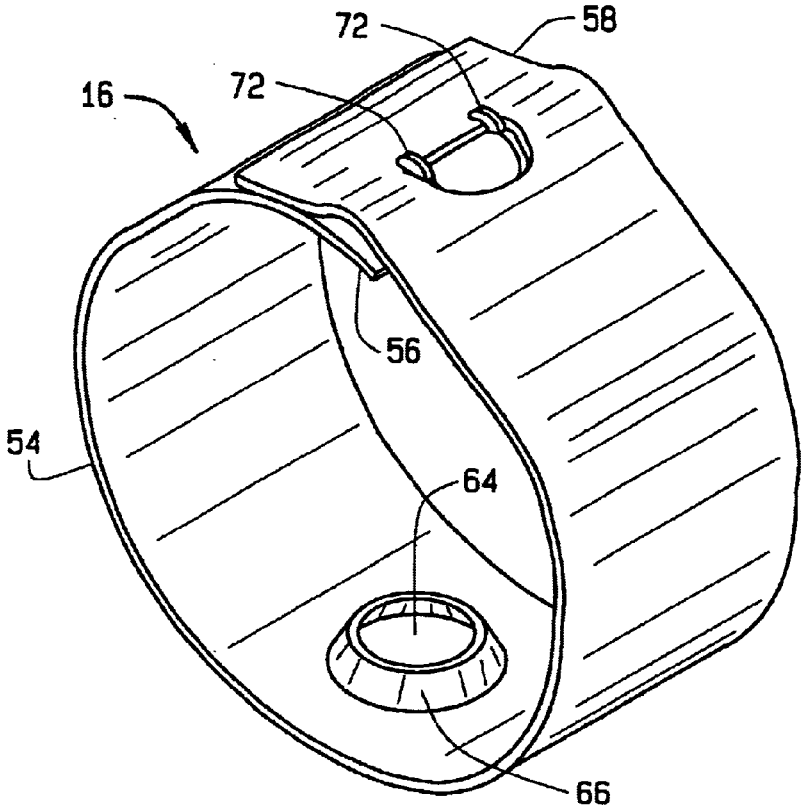
FIG. 1 is a perspective view of the one-piece unitary occluder according to the present invention.

Referring to the drawings, the preferred embodiment of the one-piece unitary occluder of the present invention is illustrated and generally indicated as 16 in FIG. 1. The one-piece unitary occluder 16 is used in a fluid administration system 10 having a tube assembly 14 coupled to a pump 12 (FIG. 8).

Figure 8:
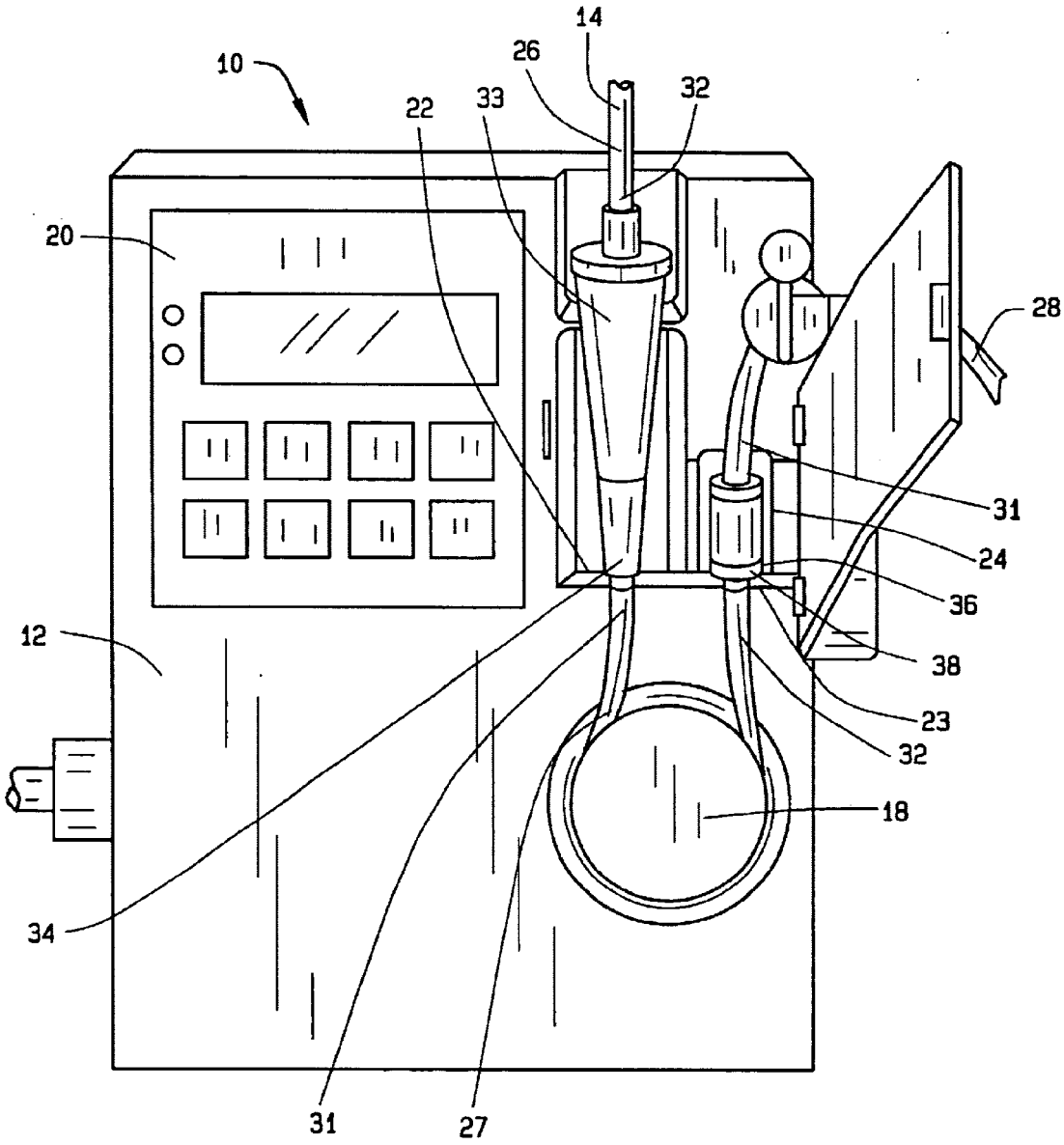
FIG. 8 is a perspective view of a clinical peristaltic pump having the one-piece unitary occluder disposed within the occluder receptacle and fitted about a portion of the tubing administration set according to the present invention.

The pump 12 of the present invention is preferably a clinical peristaltic pump as shown in FIG. 8. Of course, one skilled in the art can best appreciate that a variety of other pumps such as a linear peristaltic pump and the like may be utilized without the departing from the novel aspects of the present invention. Specifically, pump 12 includes a rotor 18 and a readout 20 adjacent rotor 18 which permits an operator to monitor and adjust the rotation rate of rotor 18. Also, adjacent rotor 18 is a first shoulder 22, a second shoulder 23, and a recess 24. The pump 12 also includes a cover 25 which is pivotably attached over shoulders 22, 23, and recess 24. The purpose of which will be discussed in further detail below.

The tube assembly 14 includes a first tube segment 26 in communication with a second tube segment 27 which is in communication with a third tube segment 28. Each tube segment 26, 27, and 28 has a distal end 31 and a proximal end 32. Connected to distal end 31 first tube segment 26 is a fluid source (not shown). A drip chamber 33 having an abutment surface 34 interconnects proximal end 32 of first tube segment 26 with distal end 31 of second tube segment 27, while the proximal end 32 of second tube segment 27 is interconnected to distal end 31 of third tube segment 28 by a coupling 36 lo having an external flange 38. Finally, third tube segment 28 terminates at a proximal end 32 which is connected to a patient (not shown).

The abutment surface 34 of drip chamber 33 and external flange of coupling 36 are sized and shaped to be captured by first shoulder 22 and second shoulder 23, respectively of pump 12, while one-piece unitary occluder 16 is partially received within recess 24. Abutment surface 34 is spaced apart from external flange 38 by the length of second tube segment 27. Preferably, this length permits abutment surface 34 and external flange 38 to be properly engaged with the first shoulder 22 and second shoulder 23, respectively, while also engaging and properly stretching second tube segment 27 about rotor 18. One skilled in the art can best appreciate that the amount that the second tube segment 27 is stretched about rotor 18 may be varied by altering the length of the second tube segment 27. Finally, each tube segment 26, 27 and 28 has a lumen (not shown) through which fluid may pass from the fluid source and out proximal end 32 of third tube segment 28.

Figure 13:
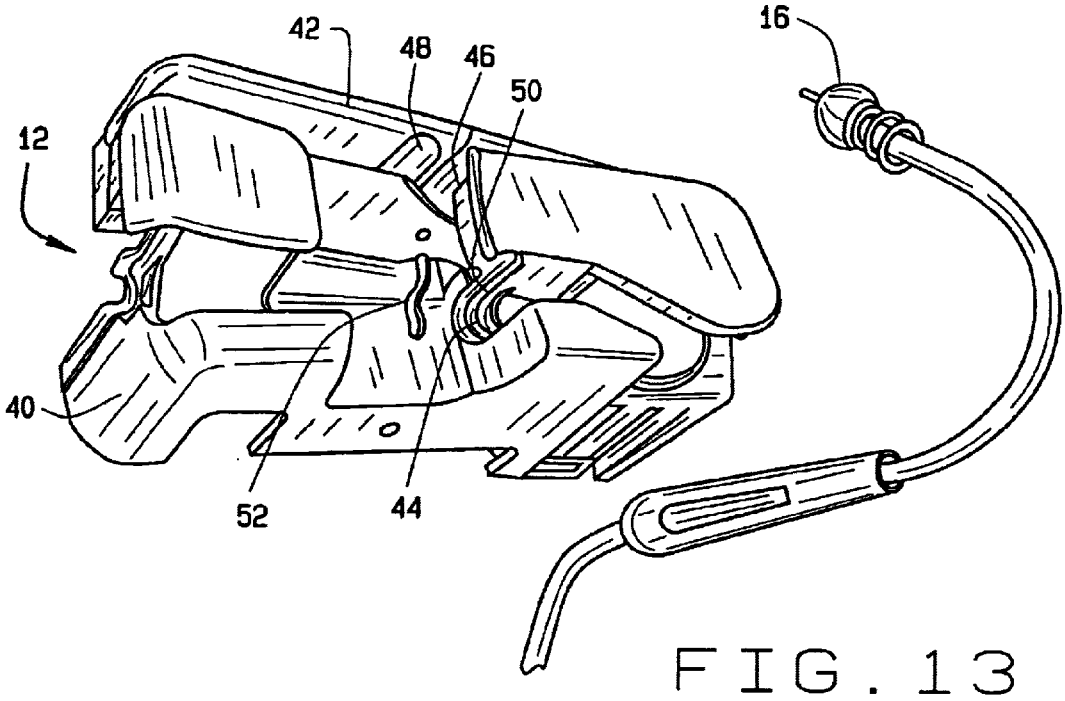
FIG. 13 is a perspective view of an ambulatory peristaltic pump having the one-piece unitary occluder disposed within the occluder receptacle and fitted about a portion of the tubing administration set according to the present invention.

In an alternative embodiment, as shown in FIG. 13, the pump 12 may be an ambulatory peristaltic pump having body 40, a rotor 18 and a swing arm 42 pivotable between an open position and a closed position. The pump 12 also includes a pair of shoulders 44, 46 with one shoulder 44 formed on the body 40 and the other shoulder 46 located on the swing arm 42. Finally, the pump 12 includes a receptacle 48 having a hole 50 with a rod 52 fitted therethrough for engagement with occluder 16.

Figure 2:
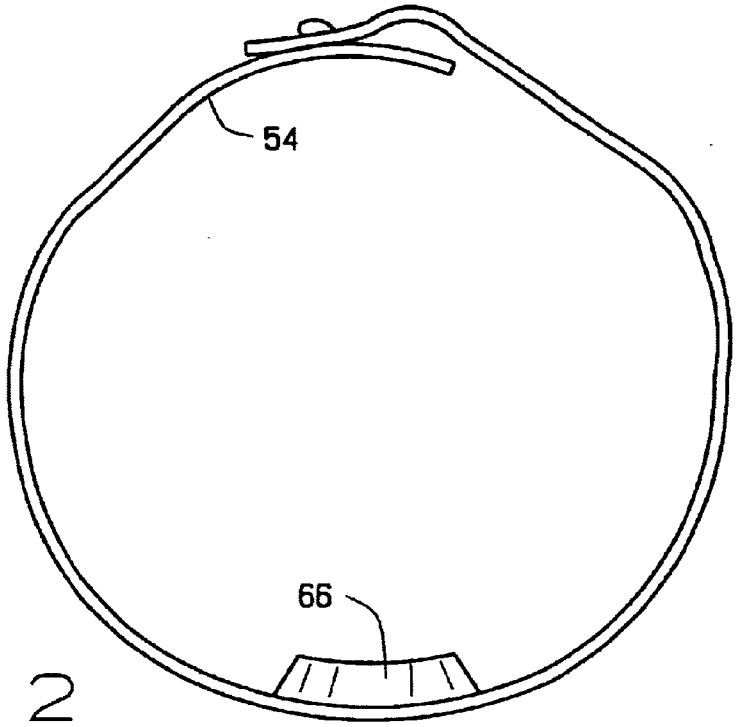
FIG. 2 is a side elevational view of the one-piece unitary occluder according to the present invention.
Figure 4:
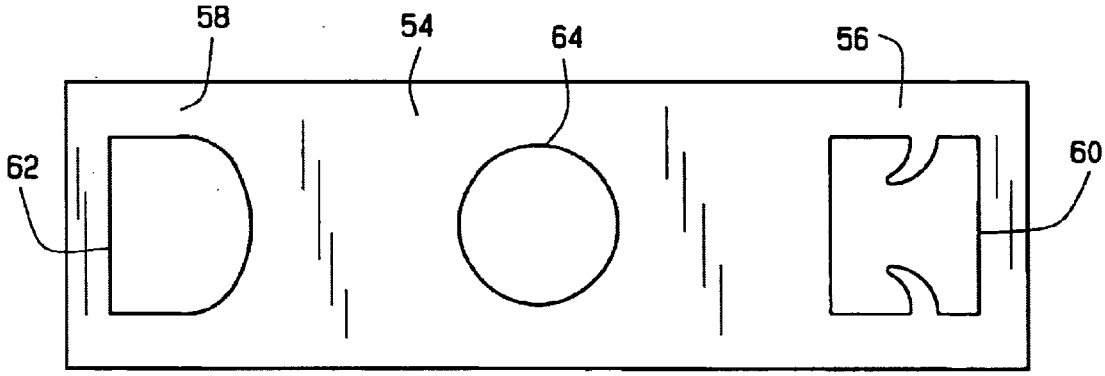
FIG. 4 is a top plan view of an unassembled one-piece unitary occluder after a pair of openings and an aperture are punched therethrough during manufacturing according to the present invention.

As illustrated in FIG. 1, one unique aspect of the present invention is the one-piece occluder 16 which comprises a unitary body 54 having a pair of end portions 56, 58 with openings 60, 62 (as seen in FIG. 4) formed through each of the end portions 56, 58, respectively. End portion 56 is overlaid by end portion 58 so that the one-piece occluder 16 has a generally cylindrical shape when viewed from the side (as shown in FIG. 2). The body 54 also includes an aperture 64 which is located approximately at the midpoint between the pair of openings 60, 62. The openings 60, 62 and aperture 64 are sized to receive a portion of the tube assembly 14 therethrough.

Figure 3:
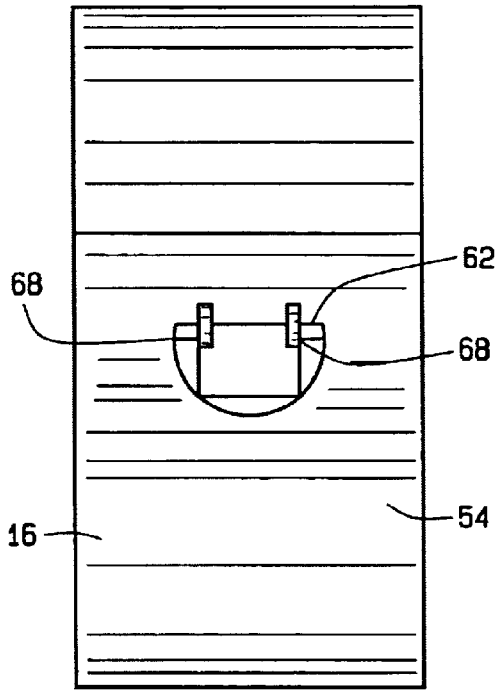
FIG. 3 is a front elevational of the one-piece unitary occluder according to the present invention.

Referring to FIG. 2, a shoulder 66 is formed about the aperture 64 and extends inwardly within body 54 and is sized and shaped to couple with coupling 36 so that the occluder 16 is properly located along a portion of tube 14. As shown in FIG. 3, a pair of hooks 68 extend outwardly away from body 54. Each hook 68 captures opening 62 to retain the one-piece occluder 16 in a loaded, or coiled, position with openings 60, 62 in an aligned configuration relative to aperture 64. Although two hooks 68 have been disclosed in a preferred embodiment, one skilled in the art can best appreciate that any number of hooks may be utilized without departing from the unique aspects of the present invention. Finally, end portion 58 includes a V-shaped bend 70 (FIG.2) pointing radially inward which is adapted to urge end portion 56 radially outward once hooks 68 are disengaged from opening 62.

Uniquely, the one-piece occluder 16 of the present invention has a one-piece unitary design which may be manufactured in a simple and cost effective manner. Although a variety of processes may be utilized to manufacture the one-piece unitary occluder 16, the preferred method of manufacturing the present invention is by a progressive stamping operation. However, one skilled in the art can appreciate that a variety of other manufacturing methods may be utilized without departing from the unique aspects of this invention. The one-piece occluder 16 is formed from a substantially elastic material with sufficient shape memory to regain a given configuration once an applied force is removed, such as copper or other similar metal materials.

Figure 5:
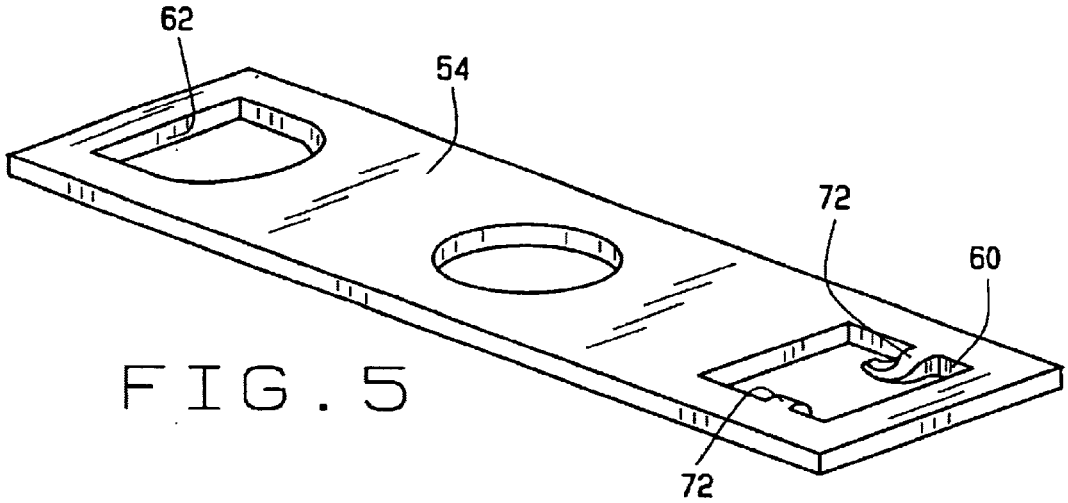
FIG. 5 is a perspective view of an unassembled one-piece occluder after a pair of hooks are bent upward during manufacturing according to the present invention.
Figure 6:
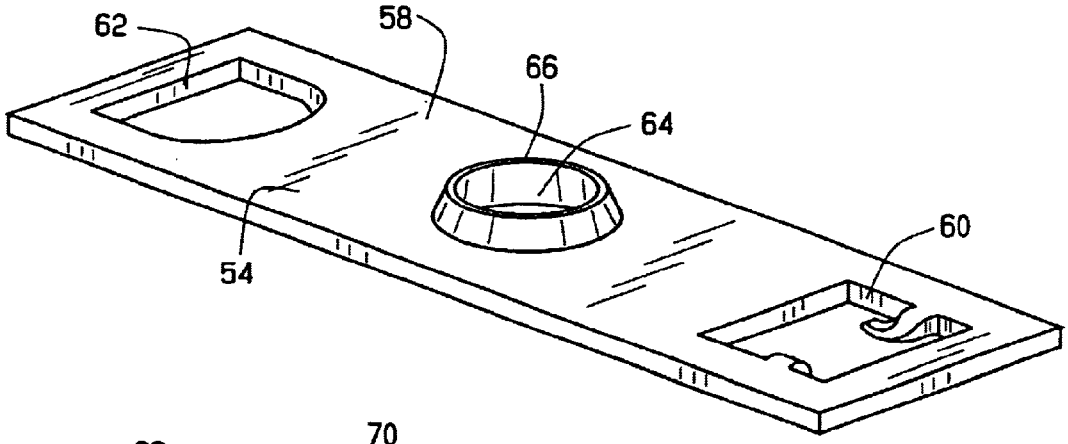
FIG. 6 is a perspective view of an unassembled one-piece occluder with the collar formed about the aperture during manufacturing according to the present invention.
Figure 7:
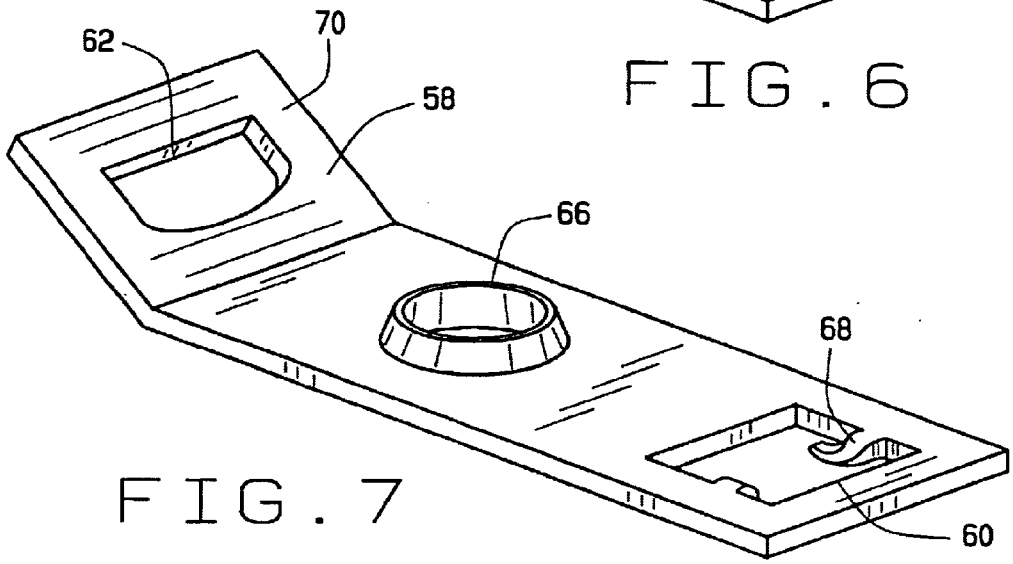
FIG. 7 is a perspective view of an unassembled one-piece occluder after the other end portion is bent into V-shape during manufacturing according to the present invention.

The process of manufacturing the present invention includes the steps of cutting a body 54 from a sheet or band (not shown), of suitable material to an appropriate length. Next, as illustrated in FIG. 4, the pair of openings 60, 62 and the aperture 64 are punched through the body with a pair of tabs 72 formed adjacent opening 60. After the openings 60, 62 and aperture 64 are formed, each tab 72 is bent downwardly relative to the body 54, as shown in FIG. 5 to form hooks 68. Referring to FIG. 6, a shoulder 66 is stamped about the aperture 64 which extends in an upward direction relative to the body 54. With reference to FIG. 7, end portion 58 is bent into a generally V-shaped bend 70. Referring back to FIG. 1, body 54 is rolled into a generally cylindrical shape with end portion 58 overlapping at least a portion of end portion 56 with shoulder 66 extending inward while hooks 68 extending outward. Finally, hooks 68 are engaged with opening 62 so that the openings 60, 62 are diametrically aligned with aperture 64.

Figure 9:
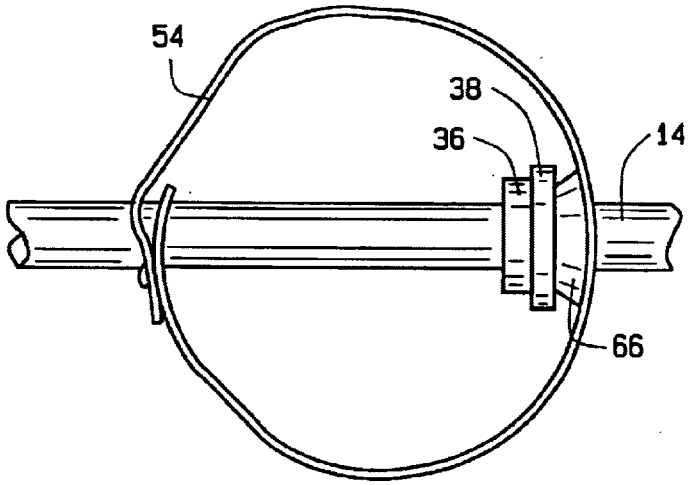
FIG. 9 is a side elevational view of the one-piece unitary occluder fitted about a portion of the tubing administration set in a latched and aligned position with the openings aligned with the aperture according to the present invention.
Figure 10:
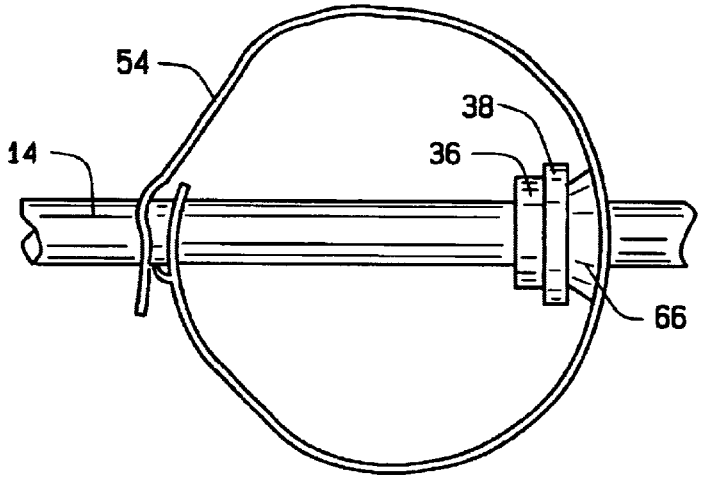
FIG. 10 is a side elevational view of the one-piece unitary occluder fitted about a portion of the tubing administration set in an unlatched and aligned position with the openings aligned with the aperture according to the present invention.
Figure 11:
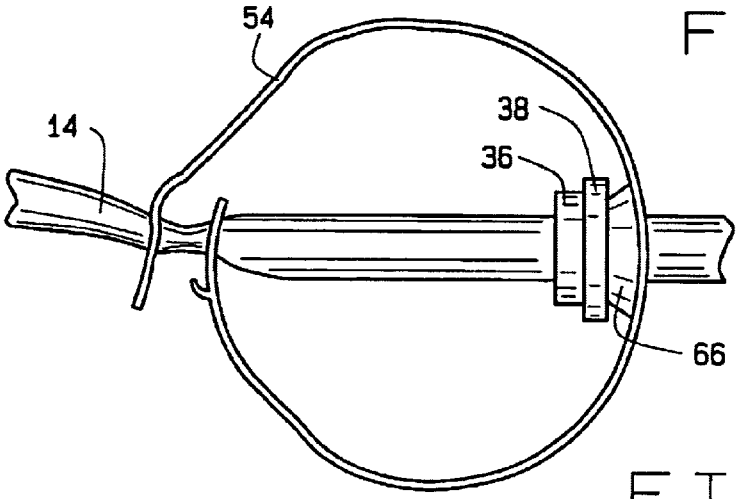
FIG. 11 is a side elevational view of the one-piece unitary occluder fitted about a portion of the tubing administration set in an unlatched and misaligned position with the openings misaligned relative to the aperture according to the present invention.

In operation, a user of the present invention first engages abutment surface 34 of drip chamber 33 with the first shoulder 22 and then wraps second tube segment 27 about rotor 18 of pump 12. Once second tube segment 27 is wrapped about rotor 18, coupling 36 is engaged with the second shoulder 23 and the one-piece occluder 16 is fitted within recess 24 with a portion thereof extending upwardly from recess 24. As shown in FIG. 9, hooks 68 engage opening 62 in order to retain openings 60, 62 in alignment with aperture 64 during shipment of tube assembly 14. With reference to FIG. 10, when the cover 25 is in a closed position overlaying shoulders 22, 23, and recess 24, the one-piece occluder 16 is biased by cover 25 and forced to coil inwardly upon itself until hooks 68 are disengaged from opening 62. In an alternative embodiment shown in FIG. 13, the occluder 16 is forced to coil inwardly upon itself by squeezing the occluder 16 between the rod 52 and swing arm 42. Because hooks 68 are free of opening 62, end portion 58 springs radially outward away from end portion 56 due to the radial outward force created by the abutment of V-shaped bend 70 with end portion 56 which allows hooks 68 to disengage from opening 62. When hooks 68 disengage from opening 62, the one-piece occluder 16 uncoils outwardly under its own spring force until abutting the cover 25, or swing arm 42 which maintains openings 60, 62 in an aligned orientation relative to aperture 64. As best appreciated with reference to FIG. 11, if cover 25, or swing arm 42, happens to be biased into an open orientation, one-piece unitary occluder 16 automatically uncoils outwardly to misalign each opening 60, 62 relative to the aperture 64 so that the portion of the second tube segment 27 of tube assembly 14 disposed through the openings 60, 62 and the aperture 64 is occluded to prevent fluid free-flow.

Figure 12:
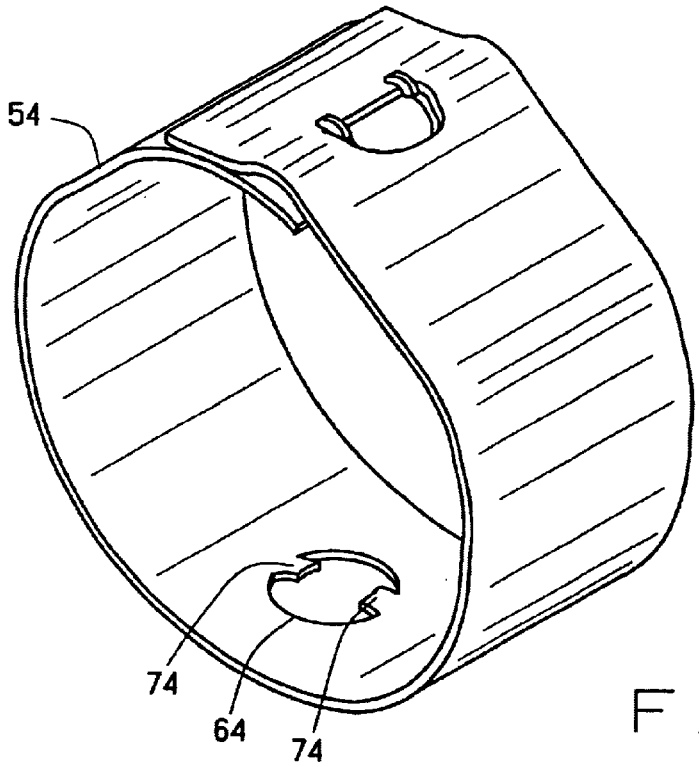
FIG. 12 is a perspective view of an alternative embodiment with a pair of tabs extending within the aperture.

In another alternative embodiment of the present invention, as best illustrated in FIG. 12, body 54 is formed with a pair of fingers 74 which extend radially inward from body 12 within aperture 64, instead of the shoulder 66, for engagement with coupling 36. Of course a variety of other members may be utilized to engage the coupling 36 without departing from the unique aspects of the present invention.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

I claim:

1. A one-piece unitary occluder comprising:

a pair of end portions at least partially overlapping, each end portion having an opening, a body including at least one hook portion proximate one of said openings for engagement with the other opening, said body further including an aperture through said body.

2. A one-piece unitary occluder according to claim 1, wherein said one-piece unitary occluder further comprises a generally cylindrical shape.

3. A one-piece unitary occluder according to claim 1, wherein at least one of said end portions further comprises a generally V-shaped portion.

4. A one-piece unitary occluder according to claim 1, wherein said at least one hook further comprises a pair of hooks.

5. A one-piece unitary occluder according to claim 1, wherein said one-piece unitary occluder is formed from a plastic material.

6. A one-piece unitary occluder according to claim 1, wherein said body further includes a shoulder disposed about said aperture.

7. A one-piece unitary occluder comprising:

a pair of ends at least partially overlapping, each end having an opening therethrough, said body further including an aperture;

means for retaining said openings in an aligned configuration relative to said aperture; and means for urging said openings into misalignment relative to said aperture.

8. A one-piece unitary occluder according to claim 7, wherein said means for retaining includes at least one hook portion disposed proximate one end for engagement with the other end.

9. A one-piece unitary occluder according to claim 8, wherein said at least one hook comprises two hooks oppositely disposed about the one opening.

10. A one-piece unitary occluder according to claim 8, wherein said means for urging comprises said body being formed from an elastic material.

11. A one-piece unitary occluder comprising:

a pair of ends at least partially overlapping, each end having an opening therethrough; and an aperture formed therethrough;

whereby said ends are movable between an aligned position having said openings aligned with said aperture and a misaligned position with said openings misaligned relative to said aperture.

12. A fluid administration system for delivering fluid from a fluid source to a patient, said fluid administration system comprising:

a pump having a rotor and a recess formed adjacent the rotor, said pump further including a cover pivotably attached over the recess;

a tube fitted about the rotor; and a one-piece unitary occluder fitted within the recess with a portion extending outwardly therefrom.

13. A fluid administration system according to claim 12, wherein said one-piece unitary occluder further comprises a generally cylindrical shape.

14. A fluid administration system according to claim 12, wherein at least one of said end portions further comprises a generally V-shaped portion.

15. A fluid administration system according to claim 12, wherein said at least one hook further comprises a pair of hooks.

16. A fluid administration system according to claim 12, wherein said one-piece unitary occluder is formed from a plastic material.

17. A fluid administration system according to claim 12, wherein said one-piece unitary occluder further includes a shoulder disposed about said aperture.

* * * * *